United States Patent [19]

Smits

[11] Patent Number: 4,620,034

[45] Date of Patent: Oct. 28, 1986

[54] PROCESS FOR THE PREPARATION OF 2-KETO-ALDONIC ACIDS

[75] Inventor: Peter C. C. Smits, Venlo, Netherlands

[73] Assignee: Akzo NV, Arnhem, Netherlands

[21] Appl. No.: 693,251

[22] Filed: Jan. 22, 1985

[30] Foreign Application Priority Data

Jan. 23, 1984 [NL] Netherlands ............... 8400203

[51] Int. Cl.$^4$ ............... C07C 51/235; C07C 51/373; C07C 59/215
[52] U.S. Cl. ............... 562/531; 562/525; 562/577
[58] Field of Search ............... 562/531, 577

[56] References Cited

U.S. PATENT DOCUMENTS 2,472,168  6/1949  Mehltretter et al. ............... 562/531
3,607,922  9/1971  Acres ............... 562/531

FOREIGN PATENT DOCUMENTS 0005779  12/1979  European Pat. Off. .
2903388  9/1979  Fed. Rep. of Germany ...... 562/531
2031884  4/1980  United Kingdom .

OTHER PUBLICATIONS

Chemical Abstracts, vol. 98, No. 13, Mar. 28, 1983, p. 637.
Heyns et al., Angew, Chem., 69, (1957), pp. 600–608.

*Primary Examiner*—Vivian Garner
*Attorney, Agent, or Firm*—Parkhurst & Oliff

[57] ABSTRACT

Preparation of 2-keto-aldonic acids, e.g., 2-keto-gluconic acid, by oxidizing an aldose, e.g. glucose, or aldonic acid in aqueous solution with molecular oxygen. Use is made of a platinum catalyst together with a catalytic amount of lead and/or bismuth and/or a compound thereof. The pH of the solution is in the range of from 4 to 12 and preferably in the range of from 7 to 9. The reaction may be carried out at a temperature in the range of 0° to 200° C. and preferably in the range of from 25° to 80° C.

6 Claims, No Drawings

PROCESS FOR THE PREPARATION OF 2-KETO-ALDONIC ACIDS

The invention relates to a process for the preparation of a 2-keto-aldonic acid from an aldose or aldonic acid.

Processes of the type indicated above have been proposed before. In U.S. Pat. No. 2,153,311, for instance, the preparation is described of 2-keto-D-gluconic acid by oxidation of D-gluconic acid with chromic acid. The oxidation is catalysed by the addition of small amounts of substances such as nickel, cerium, iron, platinum and their salts. Considering the yield in one example of 40% after a reaction time of 12 hours, it was preferred that use be made of a different starting material, such as fructose, from which according to an article by Heyns in Liebigs Ann. Chem. 558, 177 (1947) 2-keto-gluconic acid can be directly obtained by oxidation with oxygen in an aqueous alkaline solution.

Because of the higher price of the starting material it was preferred for preparation on a commercial scale, to apply fermentative oxidation of the considerably lower priced glucose.

The present invention now provides a both technically and commercially attractive process for the preparation of a 2-keto-aldonic acid from an aldose or aldonic acid by the non-fermentative route.

The invention consists in that in a process of the well-known type mentioned in the opening paragraph an aqueous solution of an aldose or aldonic acid is oxidized with molecular oxygen in the presence of a platinum catalyst together with a catalytic amount of lead and/or bismuth and/or a compound thereof.

It should be added that the catalyst system used in the process according to the present invention is known in itself from European Patent Application No. 5779. In it a process is described for the preparation of arylglyoxylic acid by catalytic oxidation with molecular oxygen in an aqueous, alkaline medium of α-hydroxyaryl acetic acid. In a comparative example (Example 10) it is demonstrated that when the catalyst system exclusively contains a noble metal (Pt), there is no longer question of oxidation of the hydroxyl group in the 2-position. Considering that glucose permits being oxidized to glucaric acid under similar reaction conditions, as shown in Example V of British Patent Specification No. 1,208,101, it was not at all to be expected that oxidation of glucose in the presence of a co-catalyst in the form of Pb and/or Bi and/or a compound thereof does not lead to oxidation of the hydroxyl group in the 6-position, but does result in oxidation of the hydroxyl group in the 2-position with formation of a 2-keto-aldonic acid, or in fact 2-keto-gluconic acid. Also unexpected was that under the reaction conditions chosen this substance displayed a remarkably high stability despite of the large number of residual OH—groups.

It should also be noted that use of the catalyst system in the oxidation with molecular oxygen of aldose, more particularly glucose, in the process of the present invention is known in itself from British Patent Specification 2,031,884. For the reaction medium, however, use is made of an organic solvent, which in the case of oxidation of glucose results in the formation of gluconic acid-δ-lactone.

The starting material used in the process of the present invention is an aldose or an aldonic acid. As examples may be mentioned: arabinose, galactose, glucose, lactose, maltose, gluconic acid and gulonic acid.

The pH of the aqueous solution to be used in the process of the invention is in the range of 4 to 12. Preference is given to a reaction medium having a pH in the range of 7 to 9.

The pH may be controlled by the gradual addition of an aqueous solution of an alkali hydroxide or carbonate. The alkali to be preferred is the hydroxide or carbonate of potassium or sodium.

The concentration of the aldose or the aldonic acid will generally be in the range of 0.5 to 60% by weight or higher. At a concentration below 0.5% by weight the further processing of the reaction mixture becomes relatively costly; and the upper limit of the concentration is governed by the prohibitively low solubility of oxygen in very strong and viscous solutions and the risk of the process equipment getting clogged as a result of crystallization. For use on an industrial scale it is generally preferred to employ an aldose or aldonic acid concentration in the range of 20 to 40% by weight.

The process according to the invention may be carried out in the entire temperature range of a liquid, aqueous phase. Consequently, reaction can take place in the range of from the solidifying point up to the boiling point of the reaction mixture. In actual practice this means that the reaction temperature range is 0° to 200° C. It is preferred that use should be made of a temperature between 25° and 80° C.

Besides the platinum catalyst to be used according to the invention there may be present one or more other noble metals, such as palladium, iridium, osmium, rhodium and ruthenium.

The noble metal may be added as such, but it is generally preferred that the metal should be applied to a carrier. Examples of suitable carrier materials include activated carbon, glassy carbon, graphite, kieselguhr, kiesel gel, aluminum oxide, calcium carbonate, magnesium carbonate, barium sulphate and organically based carrier materials.

Favorable results are obtained with activated carbon and alumina. The noble metal content of these carrier materials may vary within wide limits. Generally, favorable results may be obtained with catalyst whose noble metal content is in the range of from 0.1 to 20% by weight, preferably in the range of from 0.1 to 5% by weight. Also the amount of platinum catalyst to be used in the oxidation may vary within wide limits. The amounts to be employed depend on the desired oxidation rate, the method of aeration, the type of starting material, the form of the catalyst, the type of co-catalyst and the amount in which the cocatalyst is to be used.

The correct amount and ratio can readily be determined experimentally. Favorable results are generally obtained when the atomic ratio of lead or bismuth to platinum metal is in the range of from 2:1 to 1:20. Optimum results are obtained when the atomic ratio of lead to platinum is in the range of from 1:6 to 4:7.

The metals to be used as co-catalyst can be applied as such, i.e. in their elemental form and/or in the form of their compounds, for instance as oxides or salts of hydrogen acids, such as chloride, bromide, iodide, or as salts of inorganic oxygen-containing acids such as nitrate, nitrite, phosphite, phosphate, carbonate, perchlorate, borate, or as salts of oxygen-containing acids derived from transition metals, such as vanadate, niobate, tantalate, chromate, molybdate, wolframate, or as salts of organic aliphatic or aromatic acids, such as formiate, acetate, propionate, benzoate, salicylate, lactate, mandelate, glyoxylate, citrate or phenolate. The co-catalysts may be added to the reaction mixture in the dissolved state, in the partly dissolved state or in the undissolved state.

In addition to these co-catalysts other non-claimed elements or compounds may be present in the catalyst system to be used in the process for the invention. The co-catalysts according to the invention may have different valency values, which may still change in the course of the reaction process.

After completion of the reaction the platinum catalyst can be filtered off along with the co-catalyst and be re-used in a further oxidation reaction. The co-catalyst may be added to the reaction mixture as solid matter, preferably in a finely divided state, or in the dissolved state. The co-catalyst may already be added during the preparation of the platinum catalyst or the platinum catalyst may be impregnated with the co-catalyst. The co-catalyst also may serve as carrier material for the platinum.

The process according to the invention is generally so carried out that molecular oxygen or a molecular oxygen-containing gas, such as air, is properly contacted with the reaction medium containing the aldose and/or aldonic acid, the platinum catalyst and the co-catalyst according to the invention.

In the reaction process use will generally be made of an oxygen pressure of 0.1 MPa, but reaction will also be possible in a pressure range of from, say, 0.001 to 1 MPa. Progress of the reaction can be followed by determining the amount of oxygen taken up by the reaction mixture. Once the theoretical amount of oxygen has been taken up, the reaction rate will decrease considerably, which can therefore be considered indicative of the conclusion of the reaction. The increase of the oxygen concentration in the liquid phase is therefore indicative of the completion of the reaction.

The amount of aldonic acid and 2 keto-aldonic acid formed in the course of the reaction process can be determined by liquid chromatographic analysis. At conclusion of the reaction the noble metal catalyst is isolated from the reaction mixture along with the non-dissolved co-catalyst, for instance by filtration.

The invention will be further described in the following examples, which are of course not to be regarded as limiting the scope of the present invention.

PREPARATION OF CATALYST

The catalyst was prepared by a method described by Zelinskii (Zelinskii, N. D., Turowa-Pollak, M. B., Ber.,58, 1298 (1925); Liberman, A. L., Schabel, K. H., Vasina, T. V., Kazanskki, B. A., Kinet-Katal.2, 446 (1961)). A solution of 10 g of hexachloroplatinic acid ($H_2PtCl_6 \cdot 6H_2O$) in 100 ml of water was added to 72 g of activated carbon (sieve fraction 50–100 μm), after which 100 ml of water were added to entirely wet the carbon. During the adsorption at room temperature of the platinic acid on the carrier nitrogen was bubbled through the suspension. After the adsorption equilibrium had been attained (5 hours), the suspension was cooled to 0° C. To the suspension were added 170 ml of a 35%-formaldehyde solution. Subsequently, over a period of 16 hours 90 ml of a 30%-KOH solution were added dropwise, as a result of which the platinum compound was reduced to platinum metal. After filtration of the catalyst it was washed with water until the filtrate was neutral. After drying at 50° C. under reduced pressure a Pt/C catalyst was obtained having a platinum content of about 5% by weight.

ADDING CO-CATALYST TO PT/C CATALYST

To part of the Pt/C catalyst thus prepared some amount of lead (II) acetate solution was added. The mixture was stirred for 1 hour at room temperature, followed by adding an $Na_3PO_4$ solution in an amount such that the number of moles of phosphate corresponded to 1.2 times the number of moles of Pb. After stirring for 1 hour and standing overnight the $Pb_3(PO_4)_2$/Pt/C catalyst was filtered off, washed with water and dried at 50° C. under reduced pressure.

The same procedure was used for preparing a $Pb(OH)_2$/Pt/C catalyst, except that after adsorption of lead (II) acetate NaOH was added instead of $Na_3PO_4$.

PREPARATION OF $PB/PT/AL_2O_3$ CATALYST

In the preparation use was made of a commercially available starting material in the form of 5% Pt-containing $Al_2O_3$ pellets which were pulverized in a mortar. The sieve fraction with a particle size between 105 and 210μ was reduced with 5 ml of formalin in a nitrogen medium at pH 10. To the resulting catalyst lead in the form of $Pb_3(PO_4)_2$ was applied in the same way as indicated hereinbefore in the preparation of the Pb/Pt/C catalyst. The atomic ratio Pb/Pt was 0.5.

COMPARATIVE EXAMPLE I

In a reactor vessel provided with a stirrer, a thermometer, a pH electrode and a sampling position there were introduced 6.85 g of gluconic acid (34.93 mmoles), 7.9 g of Pt/C catalyst, sodium hydroxide to a pH=8 and water to a volume of 197.8 ml. The reaction vessel was heated to a temperature of 55° C. with nitrogen being flushed through. Subsequently, oxygen was passed through the reaction vessel. The pH of the solution was kept at a constant value (PH=8) with the aid of an automatic titrator and a sodium hydroxide solution. The samples taken at regular intervals were subjected to liquid chromatographic analysis. After 5 hours the reaction was terminated. Analysis showed that practically no 2-keto-D-gluconic acid had formed and that a large proportion of the D-gluconic acid had been converted, D-glucaric acid being the main product, along with oxalic acid and other sideproducts.

COMPARATIVE EXAMPLE II

The same procedure was used as in Comparative Example I, except that use was made of a commercially available Pt/C catalyst of the F 196 RA/W type marketed by Degussa. Use was made of 4.81 g (24.52 mmoles) of gluconic acid and 6 g of catalyst. The reaction mixture was brought to pH=8 with sodium hydroxide and diluted with water to 150 ml. After a reaction time of 1 hour practically all of the gluconic acid had been converted into D-glucaric acid and to a lesser extent into oxalic acid.

EXAMPLE I

In this example use was made of the same catalyst as in Comparative Example II, with the exception that as co-catalyst $Pb(OH)_2$ was added in an amount such that the atomic ratio of lead to platinum was 0.5. Use was made of 4.74 g (24.2 mmoles) of gluconic acid and 6 g of catalyst. The reaction mixture was again brought to pH=8 with sodium hydroxide and diluted with water to 150 ml. In the course of the reaction process sodium hydroxide was continuously added to keep the reaction mixture at pH=8. At regular intervals samples were taken which were examined for their composition by liquid chromatographic analysis. After a reaction time of 10 minutes a concentration of 140.9 mmoles/l was measured for 2-ketogluconic acid. After 35 minutes this concentration had decreased to 78.3 mmoles/l, whereas the oxalic acid concentration had increased to 93.4 mmoles/l.

EXAMPLE II

The experiment of Example I was repeated in such a way that as co-catalyst $Pb_3(PO_4)_2$ was used in an amount such that the automatic ratio of lead to platinum was 0.5. To a solution of 500 ml containing 86.6 mmoles (16.97 g) of D-gluconic acid there were added 20 g of catalyst. The reaction temperature was 55° C. After a reaction time of 7 minutes a concentration of 128.8 mmoles/l was measured for 2-keto-D-gluconic acid. After a reaction time of 19 minutes this concentration had decreased to 109.4 mmoles/l, whereas the concentration of oxalic acid had increased from 7.6 to 44.2 mmoles/l.

EXAMPLE III

The procedure of Example II was repeated, except that use was made of D-glucose (173 mmoles/l). The catalyst concentration was 40 g/l; the volume of the reaction mixture was 150 ml. After a reaction time of 15 minutes the concentration of 2-keto-D-gluconic acid was 125.6 mmoles/l. After 23.5 minutes the concentration of 2-keto-D-gluconic acid had decreased to 103.2 mmoles/l, whereas the concentration of oxalic acid had increased to 60.9 mmoles/l.

EXAMPLE IV

The procedure of Example III was repeated in such a way that use was made of D-galactose (168.4 mmoles/l). After 20.3 minutes a reaction mixture was obtained consisting of D-galactose (0.3 mmoles/l), D-galactonic acid (16.3 mmoles/l), 5-keto-D-galactonic acid (5 mmoles/l), 2-keto-D-galactonic acid (76.4 mmoles/l), oxalic acid (51.8 mmoles/l), tartronic acid (5.3 mmoles/l) and D-galactaric acid (21.2 mmoles/l).

EXAMPLE V

The procedure of Example III was repeated in such a way that use was made of D-arabinose (161 mmoles/l). After a reaction time of over 20 minutes the reaction mixture consisted of D-arabinose (5.8 mmoles/l), D-arabinonic acid (15.1 mmoles/l), 4-keto-D-arabinonic acid (6.3 mmoles/l), 2-keto-D-arabinonic acid (83.5 mmoles/l), oxalic acid (42.1 mmoles/l), tartronic acid (13.6 mmoles/l) and D-arabinaric acid (6.9 mmoles/l).

EXAMPLE VI

The procedure of Example III was repeated in such a way that use was made of L-gulonic acid (173 mmoles/l). After a reaction time of over 15 minutes the concentration of L-gulonic acid was 0.2 mmoles/l, of 5-keto-L-gulonic acid 1.4 mmoles/l, of 2-keto-L-gulonic acid 150.3 mmoles/l, of oxalic acid 28.2 mmoles/l and of tartronic acid 1.9 mmoles/l.

EXAMPLE VII

In this example use was made of a $Bi(OH)_3/Pt/C$-catalyst prepared by adsorption of $Bi(NO_3)_3$ on the same Pt/C catalyst as was used in Comparative Example I. After adsorption of the $Bi(NO_3)_3$ on the Pt the $Bi(NO_3)_3$ with excess KOH was converted into $Bi(OH)_3$. The atomic ratio of Bi/Pt was 0.5. For oxidation with molecular oxygen use was again made of D-gluconic acid (230 mmoles/l). After a reaction time of 1 hour the reaction mixture consisted of D-gluconic acid (106.8 mmoles/l), L-guluronic acid (9.4 mmoles/l), D-glucuronic acid (10.4 mmoles/l), 2-keto-D-gluconic acid (73.2 mmoles/l), x-keto-D-gluconic acid (39.2 mmoles/l), D-glucaric acid (12.0 mmoles/l), tartaric acid (2.9 mmoles/l), tartronic acid (15.1 mmoles/l), and oxalic acid (11.6 mmoles/l).

EXAMPLE VIII

In this example use was made of the same Pt/C catalyst whose preparation is indicated in Comparative Example I. The co-catalyst used was again lead in the form of $Pb(OH)_2$. The atomic ratio of Pb/Pt was 2. The catalyst thus prepared (concentration 40 g/l) was used in the oxidation with molecular oxygen of D-gluconic acid (190 mmoles/l). The volume of the reaction mixture was 196.2 ml.

After a reaction time of 75 minutes the reaction mixture consisted of D-gluconic acid (18.9 mmoles/l), D-glucaric acid (3.4 mmoles/l), tartronic acid (7.7 mmoles/l), oxalic acid (17.8 mmoles/l), 5-keto-D-gluconic acid (4.4 mmoles/l) and 2-keto-D-gluconic acid (139.1 mmoles/l).

EXAMPLE IX

In this example use was made of the same catalyst as indicated in Example VIII, except that the atomic ratio of Pb/Pt was 1. Use of reaction mixture was indicated in Example VIII and a concentration of D-gluconic acid of 157.0 mmoles/l resulted in a maximum concentration of 2-ketogluconic acid of 137.4 mmoles/l after a reaction time of 90 minutes. The concentration of D-glucaric acid was negligibly small.

EXAMPLE X

The procedure of Example IX was repeated, except that the atomic ratio of Pb/Pt of the catalyst was 0.5.

Use of a D-gluconic acid concentration of 168.8 mmoles/l resulted in a maximum 2-keto-D-gluconic acid concentration after 90 minutes of 156.5 mmoles/l.

The concentration of D-glucaric acid was negligibly small.

EXAMPLE XI

The experiment of Example IX was repeated at an atomic ratio of Pb/Pt of the catalyst of 0.2. The volume of the reaction mixture was 500 ml. Use was made of D-gluconic acid concentration of 170.4 mmoles/l and after only 27 minutes a maximum 2-keto-gluconic acid concentration of 139.6 mmoles/l was measured.

The concentration of D-glucaric acid was negligibly small.

EXAMPLE XII

The procedure of Comparative Example II was repeated, except that before adding the D-gluconic acid properly soluble lead (II) acetate was added to the catalyst suspension in an amount such that the atomic ratio of Pb/Pt was 0.5. Use was made of D-gluconic acid (227 mmoles/l). After a reaction time of over 18 minutes the mixture substantially consisted of 2-keto-D-gluconic acid (167 mmoles/l) and only small amounts of D-gluconic acid (6.5 mmoles/l), 5-keto-D-gluconic acid (3.6 mmoles/l), oxalic acid (8.3 mmoles/l), tartronic acid (6.8 mmoles/l) and 2-keto-D-glucaric acid (15.0 mmoles/l).

The concentration of D-glucaric acid was negligibly small.

EXAMPLE XIII

The procedure of Comparative Example II was repeated, except that prior to the start of the oxidation of the D-gluconic acid a suspension of $Pb_3(PO_4)_2/C$ was added to the reaction mixture in an amount such that the concentration of $Pb_3(PO_4)_2/C$ was 40 g/l. The Pb/Pt ratio was 0.5. Use was made of D-gluconic acid (205 mmoles/l). After a reaction time of over 30 minutes the mixture was found to be composed as follows:

D-gluconic acid (14.1 mmoles/l), 5-keto-D-gluconic acid (7.3 mmoles/l), 2-keto-D-gluconic acid (128.8 mmoles/l), oxalic acid (6.0 mmoles/l), D-glucaric acid (10.0 mmoles/l) and 2-keto-D-glucaric acid (11.3 mmoles/l).

EXAMPLE XIV

In this example use was made of the $Pb/Pt/Al_2O_3$ catalyst in a concentration of 40 g/l. The volume of the reaction mixture was 150 ml.

Use of a D-gluconic acid concentration of 183.2 mmoles/l resulted in a maximum 2-keto-gluconic acid concentration after 15 minutes of 108.2 mmoles/l. The mixture obtained was moreover found to obtain small amounts of oxalic acid (14.6 mmoles/l), D-glucaric acid (9.5 mmoles/l), L-guluronic acid (4.2 mmoles/l), 5-keto-D-gluconic acid (5.7 mmoles/l) and tartronic acid (3.1 mmoles/l).

. In another experiment a Pb free $Pt/Al_2O_3$ catalyst was used. After a reaction time of 30 minutes the maximum 2-ketogluconate concentration of only 4.9 mmoles/l was reached.

I claim:

1. A process for the preparation of a 2-keto-aldonic acid from an aldose or aldonic acid, wherein a liquid aqueous solution of an aldose or aldonic acid having a pH in a range of 4–12 is oxidized with molecular oxygen at a temperature in the range of from 0 to 200° C. in the presence of a platinum catalyst together with a catalytic amount of at least one member selected from the group consisting of lead, bismuth and compounds thereof.

2. A process according to claim 1, wherein the pH of the aqueous solution of the aldose or aldonic acid is in the range of from 7 to 9.

3. A process according to claim 1, wherein the reaction is carried out at a temperature in the range of from 25° to 80° C.

4. A process according to claim 1, wherein the atomic ratio of lead or bismuth to platinum metal in said solution is in the range of from 2:1 to 1:20.

5. A process according to claim 1, wherein the atomic ratio of lead or bismuth to platinum metal in said solution is in the range of from 1:6 to 4:7.

6. A process according to claim 1, wherein the reaction is carried out at an oxygen pressure in the range of from 0.001 to 1 MPa.

* * * * *